United States Patent
Hu et al.

[11] Patent Number: 5,922,730
[45] Date of Patent: Jul. 13, 1999

[54] ALKYLATED RAPAMYCIN DERIVATIVES

[75] Inventors: David Cheng Hu, Foster City, Calif.; Alexander Aleksey Greenfield, Princeton Junction, N.J.; Thomas Joseph Caggiano, Morrisville, Pa.; Craig Eugene Caufield, Princeton Junction, N.J.

[73] Assignee: American Home Products Corporation, Madison, N.J.

[21] Appl. No.: 09/103,445

[22] Filed: Jun. 24, 1998

Related U.S. Application Data

[63] Continuation-in-part of application No. 08/926,251, Sep. 5, 1997
[60] Provisional application No. 60/025,980, Sep. 9, 1996.

[51] Int. Cl.$^6$ .................. A61K 31/445; A61K 31/435; C07D 471/04; C07D 498/18
[52] U.S. Cl. ............................ 514/291; 540/456
[58] Field of Search .............................. 540/456; 514/291

[56] References Cited

U.S. PATENT DOCUMENTS 3,929,992  12/1975  Sehgal et al. ............................ 424/122
3,993,749  11/1976  Sehgal et al. ............................ 424/122

(List continued on next page.)

FOREIGN PATENT DOCUMENTS

| 0507555 | 10/1992 | European Pat. Off. . |
| 0525960 | 2/1993 | European Pat. Off. . |
| 0532862 | 3/1993 | European Pat. Off. . |
| 9409010 | 4/1994 | WIPO . |

OTHER PUBLICATIONS

Baeder, W.L. et al., Fifth Int. Conf. Inflamm. Res. Assoc. 121 (Abstract) (1990).
Baker, H. et al., J. Antibiot. 31, 539–545 (1978).
Calne, R.Y. et al., Lancet 1183 (1978).
Dumont, F.J. et al., FASEB 3: 5256 (1989).

(List continued on next page.)

*Primary Examiner*—Mukund J. Shah
*Assistant Examiner*—Bruck Kifle
*Attorney, Agent, or Firm*—Arnold S. Milowsky

[57] ABSTRACT

This invention relates to compounds which possess immunosuppressive and/or anti tumor and/or antinflammatory activity in vivo and/or inhibit thymocyte proliferation in vitro. These compounds are therefore useful in the treaiment of transplantation rejection, autoimmune diseases such as lupus, rheumatoid ardiritis, diabetes mellitus, multiple sclerosis and in the treatment of *Candida albicans* infections and also in treatment of diseases of inflammation. These compounds are represented by the formula below

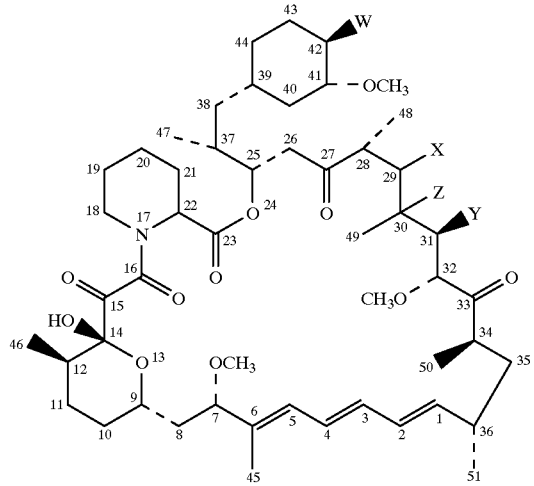

wherein W and Y are $OR^1$ and X and Z together form a bond or W and X are $OR^2$ and Y and Z together form a bond, wherein:

$R^1$ is selected from $-(CH_2)_n-Ar$ with a proviso that Ar is not phenyl,
  $-(CH_2CH_2O)_nCH_3$ with a proviso that n is greater than one,
  $-CH_2CH_2CH_2O(CH_2CH_2O)_m-CH_3$,
  $-(CH_2)_n-CH_2CH(OR^3)CH_2OR^4$ where $R^3$ and $R^4$ are H, $C_1-C_{10}$ alkyl, or $R^3$ and $R^4$ together are ethylene, methylene or dimethylmethylene;
  $-CH_2(CH_2)_n-OR^3$ with a proviso that $R^3$ is not H, $C_1-C_{10}$ alkyl, or $C(O)C_1-C_{10}$ alkyl;
  and $-CH_2(CH_2)_n-X$ where X is F, Cl, Br or I;

$R^2$ is selected from H, $C_1-C_{10}$ alkyl, $Ar(CH_2)_n-$, $C_3-C_{10}$ alkenyl, $-(CH_2CH_2O)_nCH_3$, $-CH_2CH_2CH_2O(CH_2CH_2O)_m-CH_3$, $-CH_2(CH_2)_n-OR^3$, $-CH_2(CH_2)_n-X$
where X is F, Cl, Br or I;
and $-(CH_2)_n-CH_2CH(OR^5)CH_2OR^6$ where $R^5$ and $R^6$ are selected independently from H, $C_1-C_{10}$ alkyl, $-(CH_2)_n-Ar$, $-CONH(CH_2)_n-Ar$ or $COC(CH_3)_2-(CH_2)_n-Ar$, $-COR^7$ and $-CO_2R^7$, where $R^7$ is $C_1-C_6$ alkyl, $C_2-C_6$ alkenyl, or Ar; or $R^5$ and $R^6$ together are methylene, ethylene, or dimethylmethylene;

$R^3$ and $R^4$ indepently are H, methyl, $-(CH_2)_nCH_3$, $-(CH_2)_nAr$, $-(CH_2)_nCH=CH_2$, $-C(O)R^7$, $-CO_2R^7$, $-CONH(CH_2)_nAr$ or $-C(O)C(CH_3)_2-(CH_2)_nAr$;

Ar is selected independently from phenyl, pyridinyl, quinolinyl, indolyl, furanyl, 1, 2, 3-triazolyl and tetrazolyl;

n=1–10 independently; and
m=1–5 independently, or a pharmaceutically acceptable acid addition salt where one can be formed.

4 Claims, No Drawings

U.S. PATENT DOCUMENTS

| | | | |
|---|---|---|---|
| 4,316,885 | 2/1982 | Rakhit | 424/122 |
| 4,375,464 | 3/1983 | Sehgal et al. | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 424/122 |
| 5,118,678 | 6/1992 | Kao et al. | 514/183 |
| 5,120,842 | 6/1992 | Failli et al. | 540/452 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 6/1993 | Caufield | 514/183 |
| 5,233,036 | 8/1993 | Hughes | 540/455 |
| 5,258,389 | 11/1993 | Goulet et al. | 514/291 |
| 5,260,300 | 11/1993 | Hu | 514/291 |
| 5,302,584 | 4/1994 | Kao et al. | 514/80 |
| 5,321,009 | 6/1994 | Baeder et al. | 514/4 |
| 5,358,944 | 10/1994 | Caufield | 514/183 |
| 5,362,718 | 11/1994 | Skotnicki et al. | 514/63 |
| 5,378,696 | 1/1995 | Caufield | 514/183 |
| 5,385,908 | 1/1995 | Nelson | 514/291 |
| 5,385,909 | 1/1995 | Nelson et al. | 514/291 |
| 5,385,910 | 1/1995 | Ocain et al. | 514/291 |
| 5,387,589 | 2/1995 | Kulkarni | 514/291 |
| 5,389,639 | 2/1995 | Failli et al. | 514/291 |
| 5,391,730 | 2/1995 | Skotnicki | 540/456 |
| 5,432,183 | 7/1995 | Schulte | 514/291 |
| 5,463,048 | 10/1995 | Skotnicki et al. | 540/456 |
| 5,491,231 | 2/1996 | Nelson et al. | 540/456 |
| 5,496,832 | 3/1996 | Armstrong | 514/291 |
| 5,516,781 | 5/1996 | Morris et al. | 514/291 |
| 5,559,122 | 9/1996 | Nelson et al. | 514/291 |
| 5,563,145 | 10/1996 | Failli et al. | 514/291 |
| 5,583,139 | 12/1996 | Or et al. | 514/291 |
| 5,776,943 | 7/1998 | Christians et al. | 514/291 |

OTHER PUBLICATIONS

Gregory, C. et al., J. Heart Lung Transplant. 11 (pt. 2): 197 (1992).

Martel, R.R. et al., Can. J. Physiol. Pharmacol. 55, 48 (1977).

Morris R.E. et al., Med. Sci. Res. 17: 877 (1989).

Sehgal S.N. et al., J. Antibiot. 28, 727–732 (1975).

Staruch, M.J. et al., FASEB 3: 3411 (1989).

Stepkowski, S.M. et al., Transplantation Proc. 23: 507 (1991).

Vezina, C. et al., J. Antibiot. 28, 721–726 (1975).

ALKYLATED RAPAMYCIN DERIVATIVES

This application is a continuation in part on patent application Ser. No. 08/926,251 filed Sep. 5, 1997 which claims the benefit of priority of U.S. provisional application Ser. No. 60/025,980 filed on Sep. 9, 1996.

This invention relates to compounds of formula I below or pharmaceutically acceptable salts thereof which possess immunosuppressive and/or anti tumor and/or antiinflammatey activity in vivo and/or inhibit thymocyte proliferation in vitro. These compounds are therefore useful in the tatent of transplantation rejection, autoimmune diseases such as lupus, rheumatoid arthritis, diabetes mellitus, multiple sclerosis, the treatment of Candida albicans infections, treatment of diseases of inflammation treatment of hyperproliferative vascular disease (restenosis) and in the treatment of certain human tumors.

BACKGROUND OF THE INVENTION

Rapamycin is a macrocylic triene antibiotic produced by Streptomyces hygroscopicus, which was found to have antifungal activity, particularly against Candida albicans, both in in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,929,992; and U.S. Pat. No. 3,993,749].

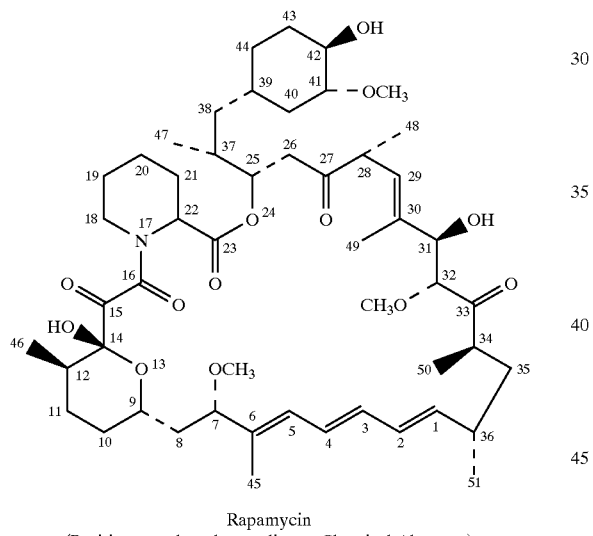

Rapamycin
(Positions numbered according to Chemical Abstracts)

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthrtis; and effectively inhibited the formation of IgE-like antibodies.

The immunosuppressive effects of rapamycin have been disclosed in FASEB 3, 3411 (1989). Rapamycin has been shown to be effective in inhibiting transplant rejection (U.S. Pat. No. 5,100,899). Cyclosporin A and FK-506, other macyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)]. U.S. Pat. No. 5,321,009 discloses a method of prophylactically preventing the onset, preventing the development, and arresting the progression of insulin-dependent diabetes mellitus by administration of rapamycin. U.S. Pat. No. 5,288,711 discloses a method of preventing or treating hypeoliferative vascular disease by administration of a combination of rapamycin and heparin. U.S. Pat. No. 5,286,730 discloses a method of treating inummointlammatory disease by treatment with rapamycin alone or in combination with cyclosporin A. U.S. Pat. No. 5,286,731 provides a method of treating immunoinflammatory bowel disease by administration of rapamycin alone or in combination with cyclosporin A.

Various structural features of rapamycin have been modified in efforts to increase the potency or specificity of pharmacological action. For instance, a number of U.S. patents disclose compounds where one or more of the hydroxy groups having normal stereochemistry at positions 14, 31, and 42 have been converted into acyl esters, sulfonyl esters, and carbamates. U.S. Pat. No. 5,023,263 discloses 42-oxo rapamycin. U.S. Pat. No. 5,258,389 discloses 31 and/or 42 O-alkyl, O-aryl, O-alkenyl, and O-alkynyl ethers of rapamycin having nomal stereochemistry at the 42 position. The PCI published application WO 94/09010 discloses 31 and/or 42 O-alkylated rapamycin analogs wherein the keto groups at positions 15 and 33 may be reduced to a hydroxyl group or a methylene group.

SUMMARY OF THE INVENTION

The compounds of this invention are represented by the following chemical formula and are novel. While a number of rapamycin analogs substituted at positions 31 and 42 have been disclosed, substitution at position 29 has not been heretofore disclosed.

The compounds useful in this invention are represented by the formula below:

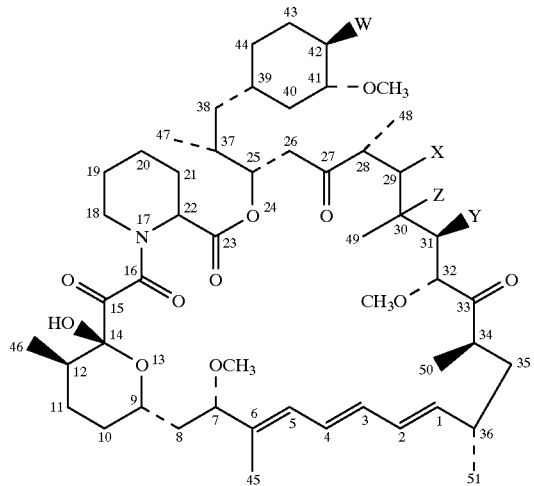

wherein W and Y are $OR^1$ and X and Z together form a bond or W and X are $OR^2$ and Y and Z together form a bond, wherein $R^1$ is selected from —$(CH_2)_n$—Ar with a proviso that Ar is not phenyl, —$(CH_2CH_2O)_n CH_3$ with a proviso that n is greater than one, —$CH_2CH_2CH_2O(CH_2CH_2O)_m$—$CH_3$, —$(CH_2)_n$—$CH_2CH(OR^3)CH_2OR^4$ where $R^3$ and $R^4$ are H, $C_1$–$C_{10}$ alkyl, or $R^3$ and $R^4$ together are ethylene, methylene or dimethylmethylene;

—CH$_2$(CH$_2$)$_n$—OR$^3$ with a proviso that R$^3$ is not H, C$_1$–C$_{10}$ alkyl, or C(O)C$_1$–C$_{10}$ alkyl;
and —CH$_2$(CH$_2$)$_n$—X where X is F, Cl, Br or I;

R$^2$ is selected from H, C$_1$–C$_{10}$ alkyl, Ar(CH$_2$)$_n$—, C$_3$–C$_{10}$ alkenyl, —(CH$_2$CH$_2$O)$_n$CH$_3$,
—CH$_2$CH$_2$CH$_2$O(CH$_2$CH$_2$)$_m$—CH$_3$, —CH$_2$(CH$_2$)$_n$—OR$^3$, —CH$_2$(CH$_2$)$_n$—X where X is F, Cl, Br or I;

and —(CH$_2$)$_n$—CH$_2$CH(OR$^5$)CH$_2$OR$^6$ where R$^5$ and R$^6$ are selected independently from H, C$_1$–C$_{10}$ alkyl, —(CH$_2$)$_n$—Ar, —CONH(CH$_2$)$_n$—Ar or COC(CH$_3$)$_2$—(CH$_2$)$_n$—Ar, —COR$^7$ and —CO$_2$R$^7$, where R$^7$ is C$_1$–C$_6$ alkyl, C$_2$–C$_6$ alkenyl, or Ar; or R$^5$ and R$^6$ together are methylene, ethylene, or dimethylmethylene;

R$^3$ and R$^4$ independently are H, methyl, —(CH$_2$)$_n$CH$_3$, —(CH$_2$)$_n$Ar, —(CH$_2$)$_n$CH=CH$_2$, —C(O)R$^7$, —CO$_2$R$^7$, —CONH(CH$_2$)$_n$Ar or —C(O)C(CH$_3$)$_2$—(CH$_2$)$_n$Ar;

Ar is selected independently from phenyl, pyridinyl, quinolinyl, indolyl, furanyl, 1, 2, 3-triazolyl and tetrazolyl;

n=1–10 independently; and m=1–5 independently.

In the above definitions of variable substituents, the termalkyl includes straight and branched chain hydrocarbons. This invention also encompasses the phamaceuticaly acceptable acid addition salts where they can be formed. Pharmaceutically acceptable acid addition salts are formed from a basic inventon compound and a pharmaceutically acceptable organic or inorganic acid including but not limited to hydrochloric acid, sulfuric acid, phosphoric acid, acetic acid, maleic acid, fumaric acid, toluenesulfonic acid, benzoic acid, succinic acid, and the like.

The compounds of this invention exhibit immunosuppressive and/or antifingal and/or antitumor and/or antinflammatory activity in vivo and/or inhibit thymocyte proliferation in vitro and are therefore useful in the treatment or inhibition of organ or tissue transplantation rejection or host vs. gaft disease, proliferative diseases such as restenosis following angioplasty procedures, autoinmune diseases such as lupus, rheumatoid arthritis, diabetes mellitus, and multiple sclerosis; fungal infections, and diseases of inflammation such as psoriasis, eczema, seborrhea, inflaat bowel disease and pulmonary inflammation such as asthma, chronic obstructive pulmonary disease, emphysema, bronchitis and the like. An invention compound was found to inhibit the growth of human breast, colon and ovarian cancer cell lines in submicromolar concentration and it is therefore expted that the invention compounds will be useful in inhibiting these and other tumors in humans.

DETAILED DESCRIPTION OF THE INVENTION

The compounds of this invention can be prepared by standard litature procedures as outlined below. Other suitable bases may be used in place of the 2,6-di-tert-butyl-4-methylpyridine and may include pyridine, lutidine, collidine, sodium hydride, or sodium carbonate.

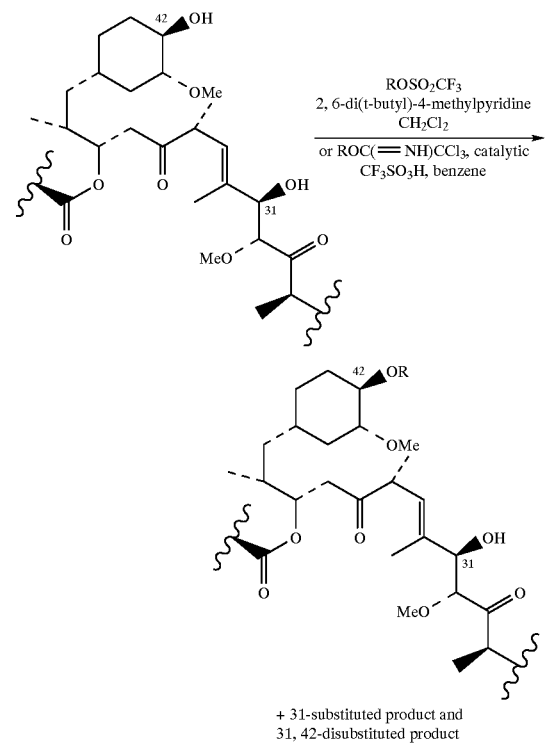

+ 31-substituted product and
31, 42-disubstituted product

Also, unexpectedly, a product was isolated (1,3-allyl rearrangement) via triflation at C-28 followed by attack by external nucleophile.

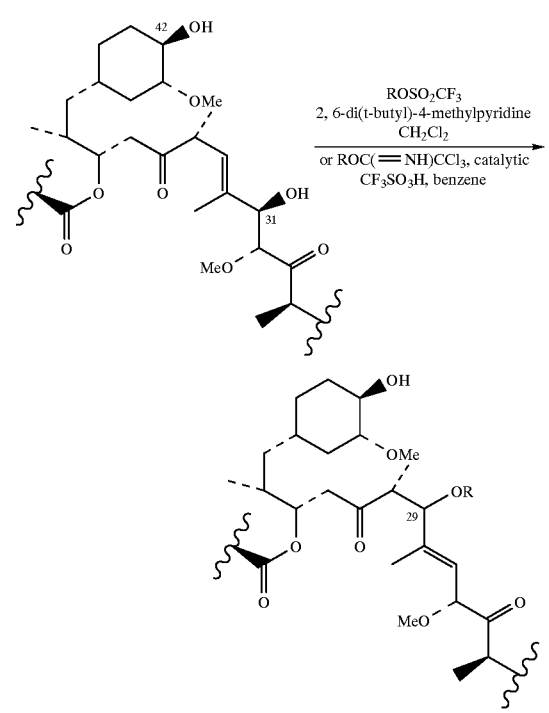

The compounds of this invention exhibit immunosuppressive and/or anneltfgal and/or anttumor and/or antinflatory activity in vivo and/or inhibit thymocyto proliferation in vitro and are therefore useful in the treatment of transplantation rejection, autoimmune diseases (i.e. lupus, rheumatoid ardtritis, diabetes menuius, multiple sclerosis), *Candida albicans* infections, and diseases of inflammation. An invention compound intibits in vitro in sub-micromolar concentrations, the growth of certain human tumor cell lines, including colon (MIP 101), breast (T47D, SKBR-3), and ovarian (A2780S) cells and therefore it is expected that compounds of this inventon will be useful in the treatment of these and other tumors.

The following procedures are included to exemplify the preparation of invention compounds and employ standard laboratory techniques known to those skilled in the art of organic systhesis.

EXAMPLE 1

29-O-Benzylrapamycin

To a solution of triflic anhydride (0.19 mL, 1.13 mmol) in dichloromethane (5.0 mL) in a round bottom flask (50 mL, flame dried) equipped with a magnetic stirer at 0° C. was added 2,6-di-t-butylmethyl pyridine (0.253 g, 1.23 mmol) portionwise. The rection mixture was degassed, and purged with nitrogen. To the solution was added a solution of benzyl alcohol (0.11 mL, 1.06 mmol, diluted in 3 mL dichloromethane) dropwise. The solution became a pale white suspension. The reaction was stirred at 0° C. for 30 min. TLC analysis indicated no residual benzyl alcohol remained. To the suspension was added another portion of 2,6-di-t-butyl-4-methyl pyridine (0.335 g, 1.63 mmol) portionwise, followed by a solution of rapamycin (0.855 g, 0.94 mmol, in 3 mL dichloromethane) dropwise. The reaction was stirred at 0° C. for 30 min, and warmed up to room temperature and stirred overnight. The reaction was quenched with saturated aqueous $NaHCO_3$, and the organic and aqueous layers were separated. The aqueous layer was extted tree times with ethyl acetate. The organic layers were combined, washed with brine, and dried over sodium sulfate. The solution was filtered and concentrated in vacuo to afford a pale yellow foam. The product mixture was separated by HPLC (40% EtOAc/hexane, Dynamax 2" silica column, 20 mL/min), and four fractions were collected The second fraction which was obtained in 12% yield was identified as 42-O-benzylrapamycin. The third fraction which was obtained in 14% yield was identified as the dihydrate of the tide compound.

$^1$H NMR (400 MHz, DMSO-$d_6$) δ 7.35 (m, 5 H, $PhCH_2O$—), 6.10–6.42 (m, 4 H, vinylic), 5.48 (q, 1 H, vinylic), 4.95 (m, 2 H, $PhCH_2O$—), 3.32 (s, 3 H. —$OCH_3$), 3.18 (s, 3 H, —$OCH_3$), 3.05 (s, 3 H, —$OCH_3$); IR (KBr, $cm^{-1}$): 3420, 2920, 1730, 1645, 1445; MS (neg. FAB): 1003.4 $[M]^-$, 652, 590, 349; Anal. Calcd. for $C_{53}H_{83}NO_{13}$·2 $H_2O$: C 66.98%, H 8.56%, N 1.39%; Found: C 66.53%, H 8.51%, N 1.70%.

Preparation of substituted alkyl triflates

To a solution of substituted alkanol (1.00 mmol) in dichloromethane (15.0 mL) in a round bottom flask (25 mL, flame dried) equipped with a magnetic stirrer at room temperature was added 2,6-di-t-butyl-4-methyl pyridine (0.60 g, 2.92 mmol). The reaction mixture was degassed, purged with nitrogen, and cooled to −78° C. To the solution was added dropwise trifluoromethanesulfonic anhydride (0.170 mL, 0.282 g, 1.00 mmol) over a period of 5 minutes. The solution became a suspension. The reaction was stirred at 0° C. for 30 minutes, then warmed up to room temperature. TLC analysis showed completion of the reaction.

General Procedure for the Preparation of 42-substituted Derivatives of Rapamycin via Nucleophilic Substitution To the solution of substituted alkyl-triflate prepared from 1 mmol of alkanol was added at room temperature (unless otherwise noted) rapamycin (914 mg, 1 mmol). The mixture was stirred between 4 and 120 h (monitoring of the extent of the reaction was carried out by TLC). When desired conversion has been achieved the reaction was quenched with saturated aqueous $NaHCO_3$, and the organic and aqueous layers were separated. The aqueous layer was extracted three times with ethyl acetate. The oraganic layers were combined, washed with brine, and dried over sodium sulfate. The solution was filtered and concentrated in vacuo to afford a product. Pure products were isolated by HPLC (normal phase—Dynarnax 2" silica column, eluent EtOAc: hexane, 20 mL/min; reversed phase—Dynamax 2" $C_{18}$ column, eluent MeCN: water, 20 mL/min. Spectroscopic analyses were used to confirm the structures.

EXAMPLE 2

42-O-(4-chlorobutyl)rapamycin

Method A. Alkanol used: 108 mg (1 mmol) of 1-chlorobutane4ol. Reaction time: 72 h at 25° C. Separation technique employed: 2" Dynamax silica column, eluent 40% EtOAc: hexane, 20 mL/min. Yield of product: 180 mg (18%).

Spectal data follows: $^1$H NMR (400 MHz, DMSO-$d_6$) δ 6.08–6.45 (m, 4 H), 3.4–3.7 (m, 8 H), 3.15 (s, 3H), 3.04 (s, 3 H). IR (KBr, $cm^{-1}$) 3420, 2930, 1715, 1650, 1620, 1460. MS (neg. FAB) 1003.4 $[M]^-$, 590.2, 411.2. Anal. calcd. for $C_{55}H_{86}NO_{13}Cl$: C 65.75%, H 8.63%, N 1.39%; Found: C 65.14 %, H 8.64%, N 1.18%.

EXAMPLE 3

42-O-(2-[2-(2-methoxy ethoxy)-ethoxy]-ethyl)-rapamycin

Method A. Alkanol used: 165 mg (1 mmol) of triethylenegycol monomethyl ether. Reaction time: 120 h at 10° C. Separation technique employed: 2" Dynamax silica column, eluent 70% EtOAc: hexane, 20 mL/min. Yield of product: 210 mg (19%).

Spectral data follows: $^1$H NMR (400 MHz, DMSO-$d_6$) δ 6.05–6.45 (m, 4 H), 3.4–3.65 (m, 12 H), 3.23 (s, 3 H), 3.14 (s, 3 H), 3.04 (s, 3 H). IR (KBr, $cm^{-1}$) 3420, 2925, 1720, 1645, 1450, MS (neg. FAB) 1059.4 $[M]^-$, 590.2, 467.2. Anal. Calcd. for $C_{58}H_{93}NO_{16}$·$H_2O$ C 64.60%, H 8.81%, N 1.28%; Found: C 63.96%, H 8.64%, N 1.15%.

Pharmacology

Immunosuppressive activity was evaluated in an in vitro standard pharmacological test procedure to measure lymphocyte proliferation (LAF), in an in vivo procedure to evaluate the survival time of a pinch skin graft, and in an in vivo procedure to determine inhibition of T-cell mediated inflammatory response (adjuvant arthritis).

The comitogen-induced thymocyte proliferation procedure (LAF) was used as an in vitro measure of the immunosuppressive effects of reresentative compounds. Briefly, cells from the thymus of normal BAUI/c mioe are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from nondrug treated controls. The results are expressed by the following ratio, or as the percent inhibition of lymphoproliferation of 1 μM.

$^3$H-control thymus cells − H$^3$-rapamycin-treated thymus cells $^3$H-control thymus cells − H$^3$-test compound-treated cells The results for the rapamycin analog (IC$_{50}$analog) and rapamycin (IC$_{50}$rapa) as well as the ratio of the ID$_{50}$s of rapamycin to the analog (R/A) are given in the table below. A ratio less than 1.0 means the analog is less potent than rapamycin.

The in vivo test procedure is designed to determine the survival time of pinch skin graft from male DBA/2 donors transplanted to male BALB/c recipients. The method is adapted from Brllingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rjection day. The mean graft survival time (MST -number of days±S.D.) of the drug treatment group is compared with the control group. Rapamycin treatment provides a mean graft survival (MST) of is 12.0±1.7 days.

The in vivo adjuvant arthritis standard pharmacological test procedure measures the abilty of test compounds to prevent immune mediated inflammation and inhibit or treat rheumatoid arthritis. The following briefly describes the test procedure used. A group of rats (male inbred Wistar Lewis rats) are pre-treated with the compound to be tested (1 h prior to antigen) and then injected with Freund's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23 and 30. The difference in paw volume (mL) from day 16 to day 0 is determined and a percent change from control is obtained. The left hind paw (uninjected paw) inflammation is caused by T-cell mediated inflammation and is recorded as percent change from control. The right hind paw inflammation, on the other hand, is caused by non-specific inflammation. Compounds were tested at a dose of 2 mg/kg. The results are expressed as the percent change in the uninjected paw at day 16 versus control; the more negative the percent change, the more potent the compound. Rapamycin provides between −70% and −90% change versus control, indicating that rapamycin treated rats have between 70–90% less immune-induced inflammation than control rats.

The following table sumrarizes the results of the compounds of this invention in these three standard test procedures.

TABLE 1

Summary of Pharmacological Test Results

| Example | Evaluation of Immunosuppressive Activity | | | | | Adjuvant Arthritis % Change |
|---|---|---|---|---|---|---|
| | LAF | | | Skin Graft | | |
| | IC$_{50}$ analog | IC$_{50}$ rapa | R/A | MST ± S.D. | | |
| 1 | 4.2 | 0.5 | 0.12 | 7.2 | 0.04 | |
| 2 | | 2.4 | 0.00 | | | |

TABLE 1-continued

Summary of Pharmacological Test Results

| Example | Evaluation of Immunosuppressive Activity | | | | | Adjuvant Arthritis % Change |
|---|---|---|---|---|---|---|
| | LAF | | | Skin Graft | | |
| | IC$_{50}$ analog | IC$_{50}$ rapa | R/A | MST ± S.D. | | |
| 3 | 1.47 | 1.1 | 0.75 | 9.8 | 0.8 | −88 |
| | 3.10 | 0.8 | 0.26 | 9.7 | 0.5 | |

The results of these standard pharmcological test procedures demonstrate immunosuppressive activity both in vitro and in vivo for the compounds of this invention. Positive ratios in the LAF test procedure indicate suppression of T cell proliferation. As transplanted pinch skin grafts are typically rejected with 6–7 days without the use of an immunosuppressive agent, the increased survival time of the skin graft when treated with the compounds of this invention further demonstrates their utility as immunosuppressive agents. The reduction of inflammatory joint swelling in the adjuvant rat model demonstrates their utility in the treatment of inflammatory diseases.

Inhibition of growth of human tumors in vitro by rapamycin analogs

The compound of Example 3 was shown to inhibit in submicromolar concentrations breast (T47D), colon (MIP 101), and ovarian (A 2780S) cancer cell lines according to the following assay procedure:

Human tumor cell lines were plated in 96-well plates (250 µL well, 1–6×10$^4$ cells/mL) in RPMI 1640 medium, containing 5% FBS (Petal Bovine Serum). Twenty-four hours after plating, drugs were added at five log concentrations (0.01–100 µg/mL). After 48 hours exposure to drugs, cells were fixed with trichloroacteic acid, and stained with Sulforhodaine B. After washing with trichloroacetic acid, bound dye was solubilized in 10 mM Tris base and Optical Density was determined using a plate reader. Under conditions of the assay, the optical density is proportional to the number of cells in the well. IC$_{50}$s (concentrations causing 50% inhibition of cell growth) were determined from the growth inhibition plots. The assay is described in details by Philip Skehan et al., J. National Cancer Institute 82, 1107–1112, 1990.

Based on the results of these standard pharmacological test procedures, the compounds are useful in the tretment of transplantation rejection such as, heart, kidney, liver, bone marrow, and skin transplants; autoimmune diseases such as lupus, rheumatoid ardritis, diabetes mellitus, myasthenia gravis, and multiple sclerosis; and diseases of inflammation such as, psoriasis, dermatitis, eczema, seborrhea, inflammatry bowel disease and pulmonary inflammation such as asthma, chronic obstructive pulmonary disease, emphysema, bronchitis and the like; proliferative diseases such as restenosis following angioplasty procedures, and fungal infections. The compounds are also expected to be useful in the treatment of breast, colon, or ovarian cancers in humans.

Pharmaceutical Composition

The compounds may be administered neat or with a pharmaceutical carrier to a mammal in need thereof. The pharmaceutical carrier may be solid or liquid and the active compound shall be a therapeutically effective amount.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilied by, for example, intramuscular, intraperitoneal or subcutaneous injection. Sterile solutions can also be administered intravenously. The compound can also be administered orally either in liquid or solid composition form. The formulated compound can further be administered intranasally through insufflation of a powder formulation, rectally or vaginally via suppositories, and topically or transdermally.

Furthermore, the formulated invention compound can be administered alone or in combination with one or more addidional immunoregluatory agents such as a coricosteroid, cyclophosphamide, rapamyucin, cyclosporin A, FK-506, OKT-3 or ATG as established by Stepkowski, Transplantation Proceedings 23: 507 (1991).

Preferably, the pharmaceutical composition is in unit dosage form, e.g. as tablets or capsules. In such form, the composition is sub-divided in unit doses containing appropriate quantities of the active ingredient; the unit dosage forms can be packaged compositions, for example, packeted powders, vials, ampoules, prefixed syringes or sachets containing liquids. The unit dosage form can be, for example, a capsule or tablet itself, or it can be the appropriate number of any such compositions in package form. The dosage to be used in the treatment must be subjectively determining by the attending physician.

What is claimed is:

1. A compound having the formula:

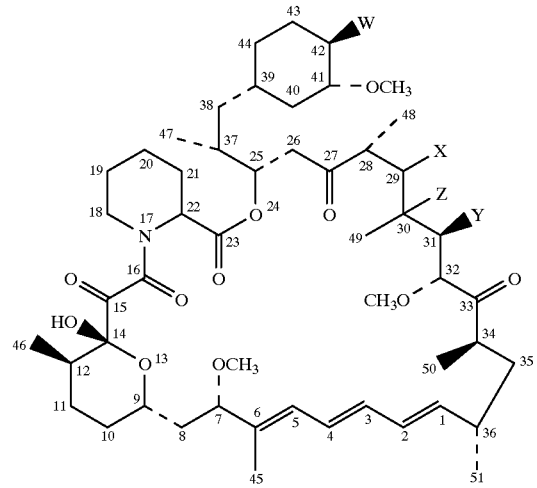

wherein W and X are $OR_2$ and Y and Z together form a bond, wherein:

$R^2$ is selected from H, $C_1$–$C_{10}$ alkyl, $Ar(CH_2)_n$—, $C_3$–$C_{10}$ alkenyl, —$(CH_2CH_2O)_nCH_3$, —$CH_2CH_2CH_2O(CH_2CH_2O)_m$—$CH_3$, —$CH_2(CH_2)_n$—$OR^3$, —$CH_2(CH_2)_n$—X where X is F, Cl, Br or I;

and —$(CH_2)_n$—$CH_2CH(OR^5)CH_2OR^6$ where $R^5$ and $R^6$ are selected independently from H, $C_1$–$C_{10}$ alkyl, —$(CH_2)_n$—Ar, —$CONH(CH_2)_n$—Ar or $COC(CH_3)_2$—$(CH_2)_n$—Ar, —$COR^7$ and —$CO_2R^7$, where $R^7$ is $C_1$–$C_6$ alkyl, $C_2$–$C_6$ alkenyl, or Ar; or $R^5$ and $R^6$ together are methylene, ethylene, or dimethylmethylene;

$R^3$ is H, methyl, —$(CH_2)_nCH_3$, —$(CH_2)_nAr$, —$(CH_2)_nCH=CH_2$,

—$C(O)R^7$, —$CO_2R^7$, —$CONH(CH_2)_nAr$ or —$C(O)C(CH_3)_2$—$(CH_2)_nAr$;

Ar is selected independendy from phenyl, pyridinyl, quinolinyl, indolyl, furanyl, 1, 2, 3-triazolyl and tetrazolyl;

n=1–10 independently; and m=1–5 independently, or a pharmaceutically acceptable acid addition salt where one can be formed.

2. A compound according to claim 1 which is 29-O-benzylrapamycin.

3. A method of ting transplantation rejection or host vs. graft disease in a mammal by administering thereto an immunosuppressing effective amount of a compound having the formula:

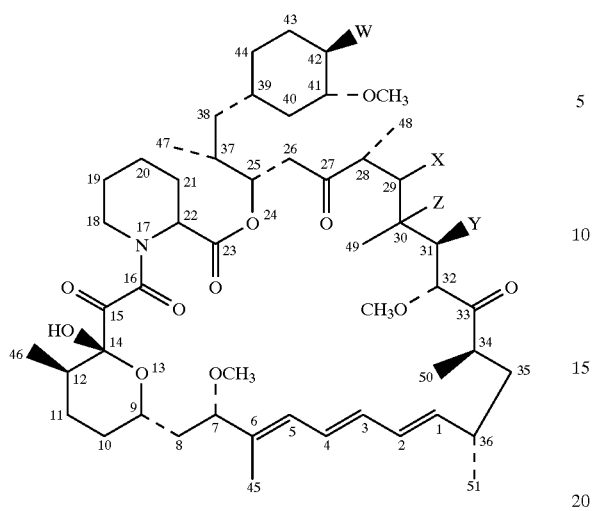

wherein W and Y are OR$^1$ and X and Z together form a bond or W and X are OR$^2$ and Y and Z together form a bond, wherein:

R$^1$ is selected from —(CH$_2$)$_n$—Ar with a proviso that Ar is not phenyl,
—(CH$_2$CH$_2$O)$_n$CH$_3$ with a proviso that n is greater than one,
—CH$_2$CH$_2$CH$_2$O (CH$_2$CH$_2$O)$_m$—CH$_3$,
—(CH$_2$)$_n$—CH$_2$CH(OR$^3$)CH$_2$OR$^4$ where R$^3$ and R$^4$ are H, C$_1$–C$_{10}$ alkyl, or R$^3$ and R$^4$ together are ethylene, methylene or dimethylmethylene;
—CH$_2$(CH$_2$)$_n$—OR$^3$ with a proviso that R$^3$ is not H, C$_1$–C$_{10}$ alkyl, or C(O)C$_1$–C$_{10}$ alkyl;

and —CH$_2$(CH$_2$)$_n$—X where X is F, Cl, Br or I;

R$^2$ is selected from H, C$_1$–C$_{10}$ alkyl, Ar(CH$_2$)$_n$—, C$_3$–C$_{10}$ alkenyl, —(CH$_2$CH$_2$O )$_n$CH$_3$,
—CH$_2$CH$_2$CH$_2$O(CH$_2$CH$_2$O)$_m$—CH$_3$, —CH$_2$(CH$_2$)$_n$—OR$^3$, —CH$_2$(CH$_2$)$_n$—X
where X is F, Cl, Br or I;
and —(CH$_2$)$_n$—CH$_2$CH(OR$^5$)CH$_2$OR$^6$ where R$^5$ and R$^6$ are selected independently from H, C$_1$–C$_{10}$ alkyl, —(CH$_2$)$_n$—Ar, —CONH(CH$_2$)$_n$—Ar or COC(CH$_3$)$_2$—(CH$_2$)$_n$—Ar; —COR$^7$ and —CO$_2$R$^7$, where R$^7$ is C$_1$–C$_6$ alkyl, C$_2$–C$_6$ alkenyl, or Ar, or R$^5$ and R$^6$ together are methylene, ethylene, or dimethylmethylene;

R$^3$ and R$^4$ indepently are H, methyl, —(CH$_2$)$_n$—CH$_3$, —(CH$_2$)$_n$Ar, —(CH$_2$)$_n$CH=CH$_2$, —C(O)R$^7$, —CO$_2$R$^7$, —CONH(CH$_2$)$_n$Ar or —C(O)C(CH$_3$)$_2$—(CH$_2$)$_n$Ar;

Ar is selected independently from phenyl, pyridinyl, quinolinyl, indolyl, furanyl, 1, 2, 3-triazolyl and tetrazolyl;

n=1–10 independently; and m=1–5 independently, or a pharmaceutically acceptable acid addition salt where one can be formed.

4. A pharmaceutical composition comprising a pharmaceutically acceptable carrier and a therapeutically effective amount of a compound of the formula:

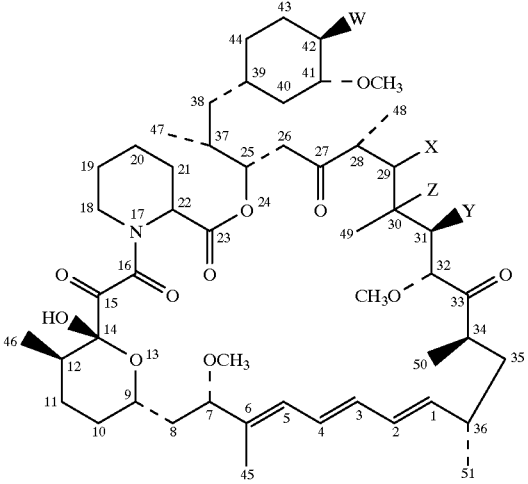

wherein W and X are OR$^2$ and Y and Z together form a bond, wherein:

R$^2$ is selected from H, C$_1$–C$_{10}$ alkyl, Ar(CH$_2$)$_n$-, C$_3$–C$_{10}$ alkenyl, —(CH$_2$CH$_2$O )$_n$CH$_3$, —CH$_2$CH$_2$CH$_2$O (CH$_2$CH$_2$O)$_m$—CH$_3$, —CH$_2$(CH$_2$)$_n$—OR$^3$, —CH$_2$(CH$_2$)$_n$—X
where X is F, Cl, Br or I;

and —(CH$_2$)$_n$—CH$_2$CH(OR$^5$)CH$_2$OR$^6$ where R$^5$ and R$^6$ are selected independently from H, C$_1$–C$_{10}$ alkyl, —(CH$_2$)$_n$—Ar, —CONH(CH$_2$)$_n$—Ar or COC(CH$_3$)$_2$—(CH$_2$)$_n$—Ar, —COR$^7$ and —CO$_2$R$^7$, where R$^7$ is C$_1$–C$_6$ alkyl, C$_2$–C$_6$ alkenyl, or Ar; or R$^5$ and R$^6$ together are methylene, ethylene, or dimethylmethylene;

R$^3$ is H, methyl, —(CH$_2$)$_n$CH$_3$, —(CH$_2$)$_n$Ar, —(CH$_2$)$_n$CH=CH$_2$,
—C(O)R$^7$, —CO$_2$R$^7$, —CONH(CH$_2$)$_n$Ar or —C(O)C(CH$_3$)$_2$—(CH$_2$)$_n$Ar;

Ar is selected independendy from phenyl, pyridinyl, quinolinyl, indolyl, furanyl, 1, 2, 3-triazolyl and tetrazolyl;

n=1–10 independently; and m=1–5 independently, or a pharmaceutically acceptable acid addition salt where one can be formed.

* * * * *